US009789127B2

(12) United States Patent  
Pistolesi et al.

(10) Patent No.: US 9,789,127 B2  
(45) Date of Patent: Oct. 17, 2017

(54) N-ACYL-PHOSPHATIDYL-ETHANOLAMINES AND/OR MIXTURES OF N-ACYL-ETHANOLAMINES WITH PHOSPHATIDIC ACIDS OR LYSOPHOSPHATIDIC ACIDS

(75) Inventors: Elvira Pistolesi, Milan (IT); Benvenuto Cestaro, Milan (IT)

(73) Assignee: HUNZA DI PISTOLESI ELVIRA & C. S.A.S., Milan (IT)

( * ) Notice: Subject to any disclaimer, the term of this patent is extended or adjusted under 35 U.S.C. 154(b) by 1545 days.

(21) Appl. No.: 11/858,059

(22) Filed: Sep. 19, 2007

(65) Prior Publication Data

US 2010/0179107 A1    Jul. 15, 2010

Related U.S. Application Data

(63) Continuation of application No. 10/504,124, filed as application No. PCT/EP03/01233 on Feb. 7, 2003, now abandoned.

(51) Int. Cl.

| A61K 31/661 | (2006.01) |
|---|---|
| A23J 7/00 | (2006.01) |
| A61K 8/55 | (2006.01) |
| A61K 31/164 | (2006.01) |
| A61K 31/366 | (2006.01) |
| A61Q 19/06 | (2006.01) |
| A61Q 19/08 | (2006.01) |
| A23L 33/10 | (2016.01) |

(52) U.S. Cl.
CPC ............. *A61K 31/661* (2013.01); *A23J 7/00* (2013.01); *A23L 33/10* (2016.08); *A61K 8/553* (2013.01); *A61K 31/164* (2013.01); *A61K 31/366* (2013.01); *A61Q 19/06* (2013.01); *A61Q 19/08* (2013.01); *A23V 2002/00* (2013.01)

(58) Field of Classification Search
CPC .................................................. A61K 31/661
USPC ................................................ 424/450, 489
See application file for complete search history.

(56) References Cited

U.S. PATENT DOCUMENTS

| 4,254,115 | A | 3/1981 | Dawidson et al. |
| 4,515,778 | A | 5/1985 | Kastell |
| 4,963,527 | A | 10/1990 | Bombardelli et al. |
| 5,043,323 | A | 8/1991 | Bombardelli et al. |
| 5,741,513 | A * | 4/1998 | Ghyczy et al. ............. 424/450 |
| 6,162,637 | A | 12/2000 | Lesage-Meessen et al. |
| 6,228,339 | B1 | 5/2001 | Ota et al. |
| 6,294,191 | B1 | 9/2001 | Meers et al. |
| 6,429,202 | B1 | 8/2002 | Bombardelli et al. |
| 6,479,054 | B1 | 11/2002 | Fujikawa et al. |
| 6,576,660 | B1 | 6/2003 | Liao et al. |
| 6,857,436 | B2 | 2/2005 | Labib et al. |
| 7,641,924 | B2 | 1/2010 | Mizumoto et al. |
| 8,232,418 | B1 * | 7/2012 | Bilbie et al. ................. 554/83 |
| 2001/0055627 | A1 | 12/2001 | Guthrie et al. |
| 2003/0139477 | A1 * | 7/2003 | Liao et al. ................... 514/730 |
| 2005/0002988 | A1 | 1/2005 | Mizumoto et al. |
| 2009/0143277 | A1 | 6/2009 | Mizumoto et al. |
| 2010/0266595 | A1 * | 10/2010 | Kolumam et al. ........ 424/136.1 |
| 2011/0177159 | A1 * | 7/2011 | Wu ............................... 424/450 |

FOREIGN PATENT DOCUMENTS

| EP | 0060933 A2 | 9/1982 |
| EP | 0 604 806 A | 7/1994 |
| EP | 0604806 A2 | 7/1994 |
| EP | 0620000 A2 | 10/1994 |
| EP | 1424074 A1 | 6/2004 |
| EP | 2051069 A2 | 4/2009 |
| FR | 972927 A | 2/1951 |
| GB | 2 051 069 A | 1/1981 |
| GB | 2051069 A | 1/1981 |
| JP | 63198693 A | 8/1988 |
| JP | 10084880 A | 4/1998 |
| JP | 2000219880 A | 8/2000 |
| WO | 02/080860 A2 | 9/2006 |

OTHER PUBLICATIONS

Do Carmo in Acta Med Port. May-Jun. 1991; 4(3), pp. 123-126.*
Hansen et al., "Formation of N-Acyl-phosphatidylethanolamines and N-Acylethanolamines: Proposed role in neurotoxicity", Biochemical Pharmacology, vol. 55, No. 6, Mar. 15, 1998, pp. 719-725, XP-002245165.
De Fonseca et al., "An anorexic lipid mediator regulated by feeding", Nature, vol. 414, No. 6860, 2001, pp. 209-212.
do Carmo et al., in Acta Med. Port, vol. 4 (3), pp. 123-126, 1991 (Abstract).
Nuovo, in American Family Physician, Mar. 15, 1999 (Abstract).
Pan, et al., "Dietary Fats, Membrane Phospholipids and Obesity", The Journal of Nutrition, 1994, pp. 1555-1565.
Cooper, "Abnormalities of Cell-Membrane Fluidity in the Pathogenesis of Disease", The New England Journal of Medicine, vol. 297, No. 7, Aug. 16, 1977, pp. 371-377.
Owen, et al., "Decreased Erythrocyte Membrane Fluidity and Altered Lipid Composition in Human Liver Disease", Journal of Lipid Research, vol. 23, 1982, pp. 124-132.
Schapira, et al., "Mitochondrial Function in Neurodegeneration and Ageing", Mutation Research, vol. 275, 1992, pp. 133-143.
Caimi, "Erythrocyte, Platelet and Polymorphonuclear Leukocyte Membrane Dynamic Properties in Essential Hypertension", Clinical Hemorheology and Microcirculation 17, 1997, pp. 199-208.

(Continued)

*Primary Examiner* — Gollamudi Kishore
(74) *Attorney, Agent, or Firm* — Silvia Salvadori, P.C.; Silvia Salvadori

(57) ABSTRACT

Pharmaceutical, cosmetic and dietetic compositions and functional foods, constituted by: A) phospholipid mixtures containing N-acyl-phosphatidyl-ethanolamines (NAPEs) and/or B) phospholipid mixtures containing N-acyl-ethanol amines (NAEs) together with phosphatidic acids (PAs) and/or lysophosphatidic acids (LPAs) with the proviso that said N-acyl-phosphatidyl-ethanolamines (NAPEs) do not include N-oleoyl-phosphatidyl-ethanolamine. New phosphobioflavonic complexes of NAPE or NAE with one or more bioflavonoids are also disclosed.

15 Claims, No Drawings

(56) References Cited

OTHER PUBLICATIONS

Bowling, et al., "Age-Dependent Impairment of Mitochondrial Function in Primate Brain", Journal of Neurochemistry, vol. 60, No. 5, 1993, pp. 1964-1967.
Kuroda, et al., "Secondary Bioenergetic Failure After Transient Focal Ischaemia is Due to Mitochondrial Injury", Acta Physiol. Scand., vol. 156, 1996, pp. 149-150.
Blumberg, "Considerations of the Scientific Substantiation for Antioxidant Vitamins and Beta-Carotene in Disease Prevention", The American Journal of Clinical Nutrition, 1995, pp. 1521-1526.
Reaven, "Dietary and Pharmacologic Regimens to Reduce Lipid Peroxidation in Non-Insulin-Dependent Diabetes Mellitus", The American Journal of Clinical Nutrition, 1995, pp. 1483-1489.
Freeman, et al., "Biology of Disease—Free Radicals and Tissue Injury", Laboratory Investigation, vol. 47, No. 5, 1982, pp. 412-426.
Brook, et al., "Dietary Soya Lecithin Decreases Plasma Triglyceride Levels and Inhibits Collagen- and ADP-Induced Platelet Aggregation", Biochemical Medicine and Metabolic Biology, 1986, vol. 35, pp. 31-39.
Cestaro, et al., "Interaction of GMI Ganglioside Micelles With Miultilayer Vesicles", Bulletin of Molecular Biology and Medicine, Sep. 1979, vol. 4, pp. 240-249.
Hara, Y., "Green Tea: Health Benefits and Applications", CRC Press, Taylor & Francis Group, LLC, Boca Raton, Florida, 2001, pp. 183-186.
Cestaro, et al., "Bilayer Micelle Transition in Phosphatidylcholine-Sulfatide Mixtures", Italian Journal of Biochemistry, vol. 33, No. 6, Nov.-Dec. 1984, pp. 381-391.
"#1 All Kinds of Health & Nutritional Supplements", Health. NetEzShop.com, 2000-2004, pp. 1-3.
Huang, C., "Studies on Phosphatidylcholine Vesicles, Formation and Physical Characteristics", Biochemistry, Jan. 1969, vol. 8, No. 1, pp. 344-351.
Cestaro, et al., "Fusion of Sulfatide-Containing Vesicles of Phosphatidylcholine", Eur. J. Biochem., 1983, vol. 133, pp. 229-233.
Anderson, et al, "Entrapment of Human Leukocyte Interferon in the Aqueous Interstices of Liposomes", Infection and Immunity, Mar. 1981, vol. 31, No. 3, pp. 1099-1103.
Cervato, et al., "Interactions of Insulin With Sulfatide-Containing Vesicles of Phosphatidylcholine At Different PHS", Chemistry and Physics of Lipids, vol. 43, 1987, pp. 135-146.
Gillum, et al., "N-Acylphosphatidyletanolamine, A Gut-Derived Circulating Factor Induced by Fat Ingestion, Inhibits Food Intake", Cell, vol. 135, Nov. 28, 2008, pp. 813-824.
Schmid, et al., "N-Acylated Glycerophospolipids and Their Derivatives", Prog. Lipid Res., vol. 29, pp. 1-43, 1990.
Akoka, et al., "A Phosphorus Magnetic Resonance Spectroscopy and a Differential Scanning Calorimetry Study of the Physical Properties of N-Acylphosphatidylethanolamines in Aqueous Dispersions", Chemistry and Physics of Lipids, 1988, vol. 46, pp. 43-50.
Moss, et al., "Glossary of Class Names of Organic Compounds and Reactive Intermediates Based on Structure", Pure & Appl. Chem., 1995, vol. 67, No. 8/9, pp. 1307-1310, 1327, 1347, 1357-1358, Enclosure 2, 1997, pp. 1-12.
Moss, G.P., "Nomenclature of Lipids", IUPAC-IUB Commission on Biochemical Nomenclature (CBN), http://www.chem.qmul.ac.uk/iupac/lipid/, 1976, pp. 1-2 and pp. 1-7.
Falbe, et al., "Rompp Chemie Lexikon", Georg Thieme Verlag, Stuttgart, Germany, 1992, pp. 156, with English translation of relevant portion.
Falbe, et al., "Rompp Chemie Lexikon", Georg Thieme Verlag, Stuttgart, Germany, 1992, pp. 3377, with English translation of relevant portion.
Falbe, et al., "Rompp Chemie Lexikon", Georg Thieme Verlag, Stuttgart, Germany, 1992, pp. 2189-2190, with English translation of relevant portion.
"Functional Food—Too Good Is Too Much?", http://www.gesundheit.de/ernaehrung/alternativemaehrung/functional-food-zuviel-gutes/index.html, Believed to be dated prior to Sep. 19, 2007, (With English translation) pp. 1-3.
Cullis P.R. et al., "Lipid Polymorphism and the Functional Roles of Lipids in Biological Membranes", Biochimica et Biophysica Acta, 559, 1979, pp. 399-420.
Cestaro Benvenuto, "I Liposomi: metodi di preparazione e loro applicazioni terapeutiche", Biochimica Clinica, 1990, vol. 14, No. 3, pp. 267-273 (Machine translation of Title, Introduction and final paragraph).

\* cited by examiner

N-ACYL-PHOSPHATIDYL-ETHANOLAMINES AND/OR MIXTURES OF N-ACYL-ETHANOLAMINES WITH PHOSPHATIDIC ACIDS OR LYSOPHOSPHATIDIC ACIDS

This patent application is a continuation of U.S. application Ser. No. 10/504,124 filed Feb. 10, 2005, which is a 35 USC 371 National Phase of PCT/EP03/01233 filed Feb. 7, 2003.

The present invention relates to pharmaceutical, cosmetic and dietetic compositions and functional foods, constituted by:
- A) phospholipid mixtures containing N-acyl-phosphatidyl-ethanolamines (NAPEs);

and/or
- B) phospholipid mixtures containing N-acyl-ethanolamines (NAEs) together with phosphatidic acids (PAs) and/or lysophosphatidic acids (LPAs), with the proviso that said N-acyl-phosphatidyl-ethanolamines (NAPEs) do not include N-oleoyl-phosphatidyl-ethanolamine.

Also disclosed are new phosphobioflavonic complexes of NAPE or NAE plus PA and/or LPA, with one or more bioflavonoids.

N-Acyl-ethanolamines (NAEs) and N-acyl-phosphatidyl-ethanolamines (NAPEs) are known to be present in many foods of animal and vegetable origin (H. H. Schmid et al., 1990, Prog. Lipid Res., 29, 1-43), and are particularly abundant in foods such as soy, eggs and chocolate (K. D. Chapman et al., 1993, Arch. Biochem. Biophys, 301, 21-23; E. Di Tomaso et al., 1996, Nature, 382, 677-678).

The NAEs are formed in vivo by hydrolysis of a NAPE molecule that gives rise to a mixture of NAE and a molecule of phosphatidic acid (PA) which, in turn, can be hydrolysed to lysophosphatidic acid (LPA) in accordance with the following scheme 1.

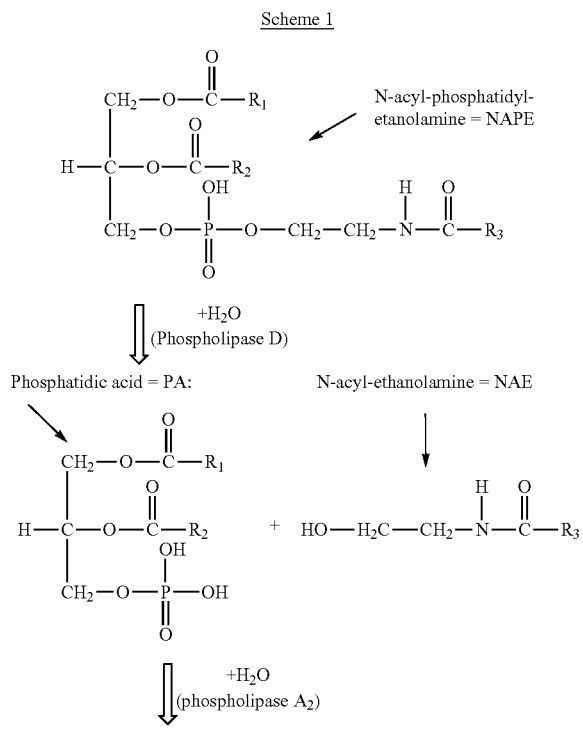

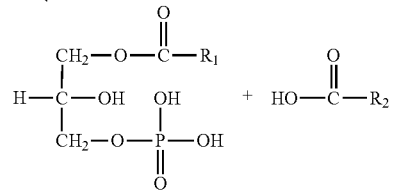

GB 2051069 discloses the anti-lipemic and anti-atherosclerotic activity of N-Oleoyl-phosphatidylethanolamine (NOPE) and excludes any significant activity of other N-acyl-derivatives.

NAEs have also been known for some time for their interesting pharmacological properties: N-arachidonoyl-ethanolamine has been demonstrated in vitro to be a cannabinoid receptor agonist (L. Hanus, 1993, J. Med. Chem., 16, 3032-3034); N-palmitoyl-ethanolamine, when administered intraperitoneally to rats, possesses anti-inflammatory and anti-anaphylactic activity (L. Facci et al., 1995, Proc. Natl. Acad. Sci. USA, 92, 3376-3380); N-palmitoyl-ethanolamine and N-stearoyl-ethanolamine have proved useful in the pharmacological treatment of inflammatory disorders resulting from degranulation of the mast cells (EP-A-0550006); they also inhibit peroxidation of the mitochondrial membranes in vitro (N. M. Gulaya et al., 1998, Chem. Phys. Lipids, 97, 49-54); N-oleoyl-ethanolamine (NOE) has a significant anorexic effect in the rat, when administered by the intraperitoneal route (F. Rodriguez de Fonseca et al., 2001, Nature, 414, 209-212). Since it is well known that NAEs are easily hydrolised to free fatty acids and ethanolamine in the gastrointestinal tract, its activity by the oral route is not expected.

The present invention relates to pharmaceutical and dietetic compositions and functional foods, constituted by:
- A) phospholipid mixtures containing N-acyl-phosphatidyl-ethanolamines (NAPEs);

and/or
- B) phospholipid mixtures containing N-acyl-ethanolamines (NAEs) together with phosphatidic acids (PAs) and/or lysophosphatidic acids (LPAs),
  with the proviso that said N-acyl-phosphatidyl-ethanolamines (NAPEs) do not include N-oleoyl-phosphatidyl-ethanolamine.

The structural formulas of NAE, PA and LPA are shown in scheme 2, wherein $R_1$, $R_2$ and $R_4$ are acyl residues of long-chain fatty acids, in particular residues of palmitic, stearic, oleic, linoleic, conjugated linoleic, linolenic, gamma-linolenic, eicosapentaenoic and docosahexanoic acids, etc.

The phospholipid mixtures may be present in the compositions of the invention in the form of their complexes with bioflavonoids. Said complexes, hereinafter called "phosphobioflavonic complexes", are a further object of the invention.

Complexes of phospholipids ouch as lecithins, phosphatidylcholine, phosphatidylethanolamine and phosphatidylserine with a number of plant extracts have been disclosed (U.S. Pat. No. 4,963,527, U.S. Pat. No. 4,895,839, EP 283713). Said complexes are reported to increase the bioavailability of the plant extract. In the phosphobioflavonic complexes of the invention, NAPE or NAE plus PA and/or LPA provide an unexpected synergism for the considered applications and do not act merely as carriers of bioflavones.

Said complexes, constituted by aggregation of the phospholipid active components (NAPE and/or NAE plus PA and/or NAE plus LPA) with one or more types of bioflavonoids, can be obtained by suspending a dry phospholipid residue under strong stirring for a few minutes at a temperature preferably between 40° and 65° C. in a hydroalcoholic solution (alcohol preferably between 70 and 90%), buffered to an acid pH (pH preferably between 3 and 5), containing a fraction of one or more types of bioflavonoids, preferably in a percentage of between 0.5 and 15% by weight of the hydroalcoholic solution. When stirring is interrupted, ethanol is partially evaporated from the resulting emulsion under vacuum and then dehydrated by spray drying, to produce a dry granular residue of phosphobioflavonic complexes.

Examples of bioflavonoids which can be used to produce these phosphobioflavonic complexes include:
a) simple polyphenols such as cinnamic, cumaric, caffeic and ferulic acids;
b) flavones such as hesperidin, naringenin and taxifolin;
c) flavonols such as kaempferol glycoside, quercetin, quercetin glycoside, myricetin and myricetin glycoside;
d) isoflavones such as genistein and daidzein;
e) proanthocyanidins such as procyanidin B1, procyanidin B2, procyanidin B3 and procyanidin C-1;
f) anthocyanidins such as pelargonidin, delphinidin, malvidin and petunidin;
g) catechins such as epicatechin, epicatechin gallate, epigallocatechin, catechins and gallocatechins;
h) tannins.

As mentioned, molecules of NAPE, NAE, PA and LPA are naturally present in the lipid fractions of many foodstuffs normally used in the human diet (soy lecithins, eggs, cocoa, meat, oily extracts of various seeds, etc.), and can easily be extracted and isolated to various degrees of purity in accordance with conventional methods. Alternatively, the NAPE and NAE molecules can be obtained by synthesis according to chemical processes which have been known for some time.

NAE can prepared from ethanolamine and the corresponding fatty acid, for example in accordance with the methods described in:
Roc E. T. et al. (1952), J. Am. Chem. Soc., 74, 3442
Chandrakumar N. S. et al. (1982), Biochim. Biophys Acta, 711, 357.

NAPE can prepared from phosphatidylethanolamine and the corresponding fatty acid chloride or anhydride, in accordance with the methods described in:
Schmid P. C. et al. (1988), J. Biol. Chem., 288 (6), 9802
Epps D. E. et al. (1980), Biochim. Biophys Acta, 618, 420
GB 2051069 B.

Another method for the preparation of NAPE by means of the enzyme phospholipase D, disclosed in U.S. Pat. No. 4,783,402, is illustrated in the scheme below:

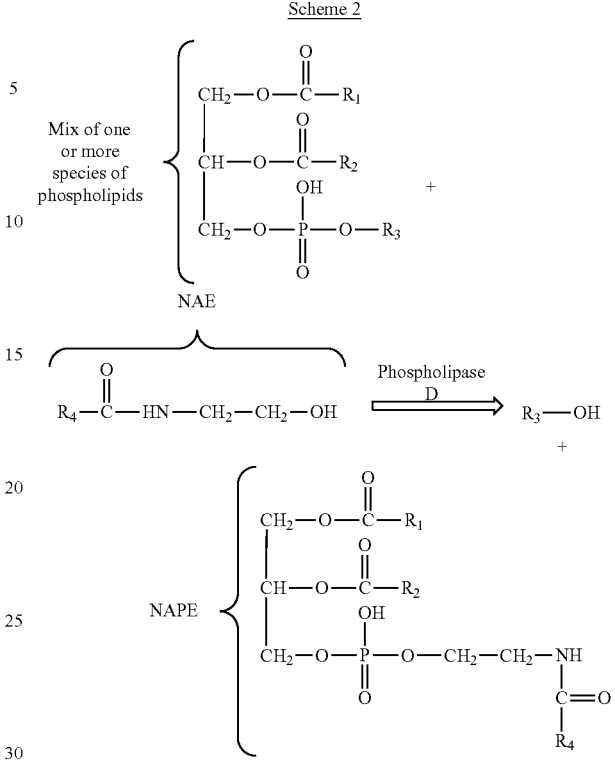

Scheme 2 wherein
$R_1$, $R_2$ and $R_4$ represent the alkyl chain of saturated, mono- or polyunsaturated fatty acids with 12-22 C atoms;
$R_3$ represents a residue of choline, ethanolamine, inositol, glycerol, serine.

The therapeutically effective doses of preparations based on NAPE and/or NAE plus PA and/or LPA vary:
a) in the case of NAPE from 0.5 to 50 mg, and preferably from 1 to 10 mg/day per kg of body weight;
b) in the case of NAE plus PA and/or LPA from 0.5 to 100 mg, and preferably from 2 to 20 mg/day/kg of body weight. In this mixture of NAE+PA and/or LPA, the percentage of NAE can vary between 1 and 70%, and preferably between 25 and 50% of the total co-mixed lipids.

The compositions of the invention may also contain other nutritional components which further implement the therapeutic properties and benefits of NAPE and/or the mixtures of NAE+PA and/or LPA. Examples of these components are:
a) vitamins and vitamin-like factors such as vitamin E, vitamin C, β-carotenes, vitamin A, vitamin D, lipoic acid and CoQ;
b) extracts of vegetables and/or medicinal plants based on mono- and diterpenes, saponins, and phytosterols;
c) proteins, peptides or aminoacids and their derivatives such as glutathione, carnosine, arginine, glutamine, carnitine, creatine and taurine;
d) trace elements and mineral salts such as Ca, Mg, Cr, Se, Va, Zn and Cu;
e) mixtures of natural amphiphilic detergents such as phospholipids and lysophospholipids; glycolipids; amphiphilic proteins; mono- and diglycerides; bile acids or salts able to incorporate NAPE and/or mixtures of NAE+PA and/or LPA in lipid emulsions of various types which help to increase their absorption and bioavailability in vivo.

The active components, stored as dehydrated granulates or powders, can be used as such or in the form of aqueous or oily solutions to make various galenical preparations such as gelatin capsules, tablets, dragées, sachets, effervescent and non-effervescent cachets, chewing gum, etc.

Said active components in the form of dehydrated granulates or powders can also be used to make various functional foods:
a) mixed with oils to make sundry dressings, sauces, creams, mayonnaise, etc;
b) mixed with flour to make bread, pasta, crackers, biscuits and other baked products;
c) added to fruit juices and squashes, mineral waters, soft drinks and other drinks;
d) added to milk and derivatives thereof (yoghurt, flans, ricotta and cheese).

The pharmaceutical or dietetic compositions of the invention have proved surprisingly active in:
a) controlling excess weight and consequently reducing the risks connected with excess weight and obesity;
b) improving the functionality of the mitochondria and the production of cell energy;
c) increasing the antioxidant defences in the various tissues;
d) improving the "fluidity" of the cell membranes and consequently the functionality of the membrane proteins (enzymes, receptors, carriers of essential nutrients and trace elements, etc.).

The preparations of the invention can therefore be used as adjuvants in the treatment of aging and many metabolic disorders connected with it (obesity and excess weight; diabetes; cerebro-degenerative disorders such as Alzheimer's disease, Parkinson's disease and senile dementia; stress, depression; tumours; menopausal syndromes; osteoporosis; prostate hypertrophy; skin aging; panniculopathy (cellulitis); and alopecia), possibly in combination with known drugs or diet supplements.

The invention therefore also concerns the use of phospholipid mixtures containing
A) N-acyl-phosphatidyl-ethanolamines (NAPEs); and/or
B) phospholipid mixtures containing N-acyl-ethanolamines (NAEs) together with phosphatidic acids (PAs) and/or lysophosphatidic acids (LPAs)

for the preparation of medicaments having anorexic activity or of medicaments or foodstuffs for the treatment of aging, obesity and excess weight; diabetes; cerebro-degenerative disorders such as Alzheimer's disease, Parkinson's disease and senile dementia; stress, depression; tumours; menopausal syndromes; osteoporosis; prostate hypertrophy; skin aging; panniculopathy (cellulitis) and alopecia.

The invention is illustrated in greater detail in the following examples.

EXAMPLE 1

98 g of $N$-linoleoyl-phosphatidylethanolamine +

1 g of $d$-$\alpha$-tocopherol + 1 g of lipoic acid.

The various compounds are dissolved and mixed in 10 volumes of chloroform:methanol (2:1, vol/vol). The solvent is evaporated under vacuum, and the resulting dry residue is re-suspended in an aqueous solution buffered to physiological pH to form an aqueous mixture of a phospholipid emulsion containing the active component (N-linoleoyl-phosphatidylethanolamine). The aqueous mixture can be frozen and dehydrated to obtain a dry residue of the phospholipid active component.

EXAMPLE 2

20 g of $N$-eicosapentaenoyl-ethanolamine +

60 g of phosphatidic acid + 80 g of soy phosphatidylcholine +

1 g of $d$-$\alpha$-tocopherol + 1 g of lipoic acid.

The various compounds are dissolved in chloroform-methanol and treated as described in example 1 to obtain an aqueous mixture of a phospholipid emulsion containing the active components (N-eicosapentaenoyl-ethanolamine and phosphatidic acid). The aqueous mixture can be frozen and dehydrated to obtain a dry phospholipid residue of the active components as described in example 1.

EXAMPLE 3

20 g of $N$-linolenoyl-ethanolamine + 40 g of lysophosphatidic acid +

1 g of $d$-$\alpha$-tocopherol + 1 g of lipoic acid.

The various compounds are dissolved in chloroform-methanol and treated as described in example 1 to obtain an aqueous mixture of a phospholipid emulsion containing the active components (N-linolenoyl-ethanolamine and phosphatidic acid). The aqueous mixture can be frozen and dehydrated to obtain a dry phospholipid residue of the active components as described in example 1.

EXAMPLE 4

20 g of $N$-gamma-linolenoyl-phosphatidylethanolamine + 80 g of a mixture of lysophospholipids (45% lysophosphatidylcholine + 35% lysophosphatidylethanolamine + 20% lysophosphatidylinositol)

1 g of $d$-$\alpha$-tocopherol + 1 g of lipoic acid.

The various compounds are dissolved in chloroform-methanol and treated as described in example 1 to obtain an aqueous mixture of a phospholipid emulsion containing the active constituent (N-gamma-linolenoyl-phosphatidylethanolamine). The aqueous mixture can be frozen and dehydrated to obtain a dry phospholipid residue of the active constituent as described in example 1.

EXAMPLE 5

20 g of a dry phospholipid residue obtained as described in examples 1-4 above +

200 g of an oily solution (olive oil, soy, corn, sunflower, borage, blackcurrant, fish or seaweed oils, or mixtures thereof).

20 g of dry phospholipid residues is slowly dissolved in 200 g of oily solution under slow, continuous stirring. The phospholipids of the dry residues are restructured in the oily solutions to form an oil-dispersed micellar organisation containing the active components.

EXAMPLE 6

100 g of a dry phospholipid residue of N-docosahexanoyl-phosphatidylethanolamine, obtained as described in example 1, is re-suspended under strong stirring for 5 minutes at 45° C. in 900 ml of a hydroalcoholic solution (75% alcohol), buffered to pH 4.5, containing 5% by weight of green tea catechins. The resulting emulsion is then cooled to room temperature and dehydrated by spray drying to form a dry granular residue of phosphobioflavonic complexes of N-docosahexanoyl-phosphatidylethanolamine and green tea catechins.

EXAMPLE 7

50 g of N-linolenoyl-ethanolamine and 50 g of lysophosphatidic acid (CLPA) are slowly added under strong stirring at 60° C. and emulsified for 10 minutes in 900 ml of a hydroalcoholic solution (85% alcohol) buffered to pH 4.0, containing 10% by weight of a mixture of catechins, epicatechins and proanthocyanidins extracted from grape seeds. When stirring is arrested, the resulting emulsion is cooled to room temperature and dehydrated by spray drying to form a dry granular residue of phosphobioflavonic complexes of N-linolenoyl-ethanolamine and grape-seed bioflavonoids.

Pharmacological and/or Dietetic Tests

A series of experimental tests on rats and clinical tests on man have been carried out to study the pharmacological and/or dietetic characteristics of the composition of the invention.

In the experimental tests, the rats were given a high-calorie, high-triglyceride, high-cholesterol diet. The following parameters were evaluated after twenty days treatment:
1) effect of the compositions on the lipoperoxide levels in the plasma, liver, brain and heart;
2) effect of the compositions on variations in body weight;
3) effect of the compositions on variations in membrane fluidity of ghost erythrocytes and plasma platelets;
4) effect of the compositions on the functionality of the hepatic mitochondria, evaluated by measuring: a) $O_2$ consumption; b) reduced glutathione; c) the potential of the mitochondrial membranes;
5) effect of the compositions on plasma levels of total cholesterol and HDL-cholesterol;
6) effect of the compositions on plasma levels of total triglycerides.

80 Male rats weighing 150-200 g each were used. The animals were divided into 8 groups of 10 animals:

$1^{st}$ group: control (C); 10 animals (control at time 0) were used as is, and 10 were given a standard high-calorie, high-fat, high-cholesterol diet for 20 days, consisting of: casein: 20%; mixture of trace elements and mineral salts: 3.5%; mixture of vitamins: 0.1%; choline bitartrate: 0.2%; cellulose: 2%; cholesterol: 0.5%; sodium cholate: 0.25%; saccharose: 58.44%, lard: 10.0% and olive oil: 4.9%.

$2^{nd}$ group: treated with N-oleoyl-ethanolamine as such (NOE); the animals were given the same diet as the controls for 20 days, except that 50 mg of NOE replaced the same quantity of olive oil (olive oil used: 4.85%).

$3^{rd}$ group: treated with N-oleoyl-phosphatidylethanolamine prepared as described in example 1 (NOPE); the animals were given the same diet as the controls for 20 days, except that 50 mg of NOPE (prepared as described in example 1) replaced the same quantity of olive oil (olive oil used: 4.85%).

$4^{th}$ group: treated with N-oleoyl-ethanolamine+phosphatidic acid prepared as described in example 2: (NOE+PA); the animals were given the same diet as the controls for 20 days, except that 400 mg of the preparation described in example 2 (containing ~50 mg of NOE and 150 mg of PA) replaced the same quantity of olive oil (olive oil used: 4.50%).

$5^{th}$ group: treated with N-oleoyl-ethanolamine+lysophosphatidic acid prepared as described in example 3: (NOE+LPA); the animals were given the same diet as the controls for 20 days, except that 150 mg of the preparation described in example 3 (containing ~50 mg of NOE and 100 mg of LPA) replaced the same quantity of olive oil (olive oil used: 4.75%).

$6^{th}$ group: treated with "phosphobioflavonic complexes" of N-oleoyl-phosphatidylethanolamine and green tea bioflavones (B.F.) prepared as described in example 6 (NOPE+B.F.). The animals were given the same diet as the controls for 20 days, except that 50 mg of NOPE and 25 mg of B.F. (corresponding to ~75 mg of the preparation described in example 6) replaced the same quantity of olive oil (olive oil used: 4.825%).

$7^{th}$ group: treated with green tea bioflavones (B.F.). The animals were given the same diet as the controls for 20 days, except that 25 mg of B.F. replaced the same quantity of olive oil (olive oil used: 4.875%).

TABLE I

Percentage variations in membrane fluidity of ghost erythrocytes and plasma platelets (expressed as a % of the control values at time 0) of the rats before and after 20 day diet treatment.

|  | Membrane fluidity (ghost erythrocytes) | Membrane fluidity (plasma platelets) |
|---|---|---|
| 1A) Control rats at time 0 | 100% | 100% |
| 1B) Control rats after a 20-day diet | 72% | 69% |
| 2) Treated rats (NOE) | 72% | 70% |
| 3) Treated rats (NOPE) | 84% | 81% |
| 4) Treated rats (NOE + PA) | 86% | 81% |
| 5) Treated rats (NOE + LPA) | 83% | 80% |
| 6) Treated rats (NOPE + B.F.) | 91% | 92% |
| 7) Treated rats (B.F.) | 73% | 70% |

TABLE II

Lipoperoxide levels [expressed as nmoles of malonyldialdehyde (MDA) per gram of tissue or per ml of plasma] in the plasma, livers, brains and hearts of the rats before and after 20 day diet treatment.

|  | MDA PLASMA | MDA LIVER | MDA BRAIN | MDA HEART |
|---|---|---|---|---|
| 1A) Control rats at time 0 | 2.5 ± 0.5 | 25.5 ± 5.9 | 55 ± 4 | 24 ± 5 |
| 1B) Control rats after a 20-day diet | 5.1 ± 0.6 | 44.2 ± 8.2 | 108 ± 6 | 45 ± 6 |
| 2) Treated rats (NOE) | 5.0 ± 0.6 | 44.1 ± 8.2 | 106 ± 7 | 44 ± 9 |
| 3) Treated rats (NOPE) | 3.8 ± 0.4 | 33.1 ± 6.5 | 85 ± 9 | 32 ± 7 |
| 4) Treated rats (NOE + PA) | 3.7 ± 0.4 | 31.8 ± 8.2 | 88 ± 7 | 34 ± 9 |
| 5) Treated rats (NOE + LPA) | 3.0 ± 0.3 | 33.5 ± 7.8 | 77 ± 5 | 34 ± 7 |
| 6) Treated rats (NOPE + B.F.) | 2.8 ± 0.3 | 29.7 ± 6.8 | 75 ± 4 | 30 ± 6 |
| 7) Treated rats (B.F.) | 5.0 ± 0.5 | 44.0 ± 7.1 | 105 ± 7 | 44 ± 7 |

TABLE III

Variation in body weight and total cholesterol, HDL cholesterol and triglyceride levels in the plasma of the rats before and after 20 day diet treatment.

| | Total cholesterol (mg $dl^{-1}$) | HDL cholesterol (mg $dl^{-1}$) | Total triglycerides (mg $dl^{-1}$) | Body weight (gm) |
|---|---|---|---|---|
| 1A) Control rats at time 0 | 35.6 ± 1.8 | 26.2 ± 1.4 | 50.2 ± 7.7 | 180 ± 12 |
| 1B) Control rats after a 20-day diet | 126.2 ± 13.5 | 29.4 ± 1.6 | 82.5 ± 9.5 | 224 ± 19 |
| 2) Treated rats (NOE) | 120.4 ± 12.7 | 28.9 ± 2.8 | 80.5 ± 6.8 | 221 ± 16 |
| 3) Treated rats (NOPE) | 110.3 ± 10.1 | 31.6 ± 3.9 | 71.4 ± 8.7 | 209 ± 18 |
| 4) Treated rats (NOE + PA) | 103.9 ± 12.4 | 29.9 ± 2.0 | 70.4 ± 10.5 | 208 ± 14 |
| 5) Treated rats (NOE + LPA) | 101.7 ± 8.9 | 32.1 ± 3.8 | 68.5 ± 7.9 | 206 ± 20 |
| 6) Treated rats (NOPE + B.F.) | 80 ± 7.5 | 31.4 ± 3.9 | 60.2 ± 6.4 | 191 ± 14 |
| 7) Treated rats (B.F.) | 123.5 ± 12.4 | 29.3 ± 1.5 | 80.7 ± 7.1 | 218 ± 17 |

TABLE IV

Variations in hepatocellular oxygen consumption, membrane potential of mitochondria and reduced hepatocellular glutathione content in control rats at time 0 and after 20 day diet treatment.

| | Hepatocellular $O_2$ consumption (umoles $O_2$/min per $10^7$ cells) | Reduced glutathione (nmoles × $10^6$ cells) | Mitochondrial membrane potential |
|---|---|---|---|
| 1A) Control rats at time 0 | 480 ± 60 | 48 ± 5 | 100% |
| 1B) Control rats after a 20-day diet | 360 ± 45 | 36 ± 4 | 68% |
| 2) Treated rats (NOE) | 368 ± 52 | 36 ± 6 | 70% |
| 3) Treated rats (NOPE) | 408 ± 62 | 41 ± 5 | 81% |
| 4) Treated rats (NOE + PA) | 412 ± 58 | 43 ± 6 | 82% |
| 5) Treated rats (NOE + LPA) | 409 ± 63 | 43 ± 8 | 83% |
| 6) Treated rats (NOPE + B.F.) | 421 ± 51 | 45 ± 5 | 88% |
| 7) Treated rats (B.F.) | 366 ± 41 | 38 ± 5 | 71% |

When the membrane fluidity of the ghost erythrocytes and plasma platelets is measured, TMA-DPH in accordance with the method described by Caimi F. et al., 1999, Thromb. Hoemost., 82 pp. 149, is used as the fluorescent probe.

Malonyldialdehyde is assayed in accordance with the procedure described by K. Yagi et al., 1982, in "Lipid Peroxides in Biology and Medicine", Academic Press, New York, 99.324-340.

Hepatocellular $O_2$ consumption, mitochondrial membrane potential and reduced glutathione content are assayed in accordance with the methods described by T. M. Hagen et al., 1999, FASEB J., 13, 99. 411.

The data set out in Tables I, II, III and IV demonstrate that administration of compositions containing the active components (NOPE; NOE+PA; NOE+LPA; NOPE+B.F.):

1) restores the membrane fluidity of ghost and platelets;
2) improves the antioxidant defences of plasma, liver, brain and heart;
3) limits excessive increases in body weight;
4) limits excessive increases in plasma cholesterol and triglyceride levels;
5) improves the functionality of the mitochondria.

These effects, obtainable by oral administration of the formulations prepared in accordance with the invention (NOPE; NOE+PA; NOE+LPA; NOPE+B.F.), are always statistically significant. It is important to note that no statistically significant benefit can be obtained by administering equivalent oral doses of N-oleoyl-ethanolamines as such.

The data set out above demonstrate the surprising synergy of action observed between NAPE and/or NAE+PA and the various bioflavonoid molecules; the therapeutic results obtainable by administering the "phosphobioflavonic complexes" of NAPE (see data set out in Tables I, II, III and IV) and NAE plus PA and/or LPA are always far higher than the sum of the benefits obtainable with single separate administrations of equivalent doses of NAPE (or NAE) and bioflavonoids.

In all the diet treatment tests carried out on man, the effects obtainable by orally the formulations claimed by the invention (NAPE; NAE+PA; NAE+LPA; NAPE+B.F. and NAE plus PA and/or LPA+B.F.) always provided highly significant results and advantages, both in preventing biological signs of aging (improvement in mitochondrial activity, better membrane fluidity, improvement in plasma antioxidant defences, and limited weight increase) and improving the clinical parameters tested in relation to prevention of aging, and many of the metabolic disorders associated therewith. It is noteworthy that also in humans no significant benefit can be obtained by administering equivalent oral doses of N-oleoyl-ethanolamine as such.

The invention claimed is:

1. A composition consisting of N-oleoyl-phosphatidyl-ethanolamine (NOPE) and green tea bioflavonoids wherein said composition is an aggregation of said N-oleoyl-phosphatidyl-ethanolamine (NOPE) and said green tea bioflavonoids, and wherein said composition is present in a hydroalcoholic solution.

2. The composition according to claim 1, wherein the aggregation is present as a dry granular residue.

3. The composition according to claim 2, wherein the bioflavonoid is a catechin selected from epicatechin, epicatechin gallate, epigallocatechin, and gallocatechin.

4. A pharmaceutical composition comprising a composition consisting of N-oleoyl-phosphatidyl-ethanolamine (NOPE) and green tea flavonoids, wherein said composition is an aggregation of said N-oleoyl-phosphatidyl-ethanolamine (NOPE) and said green tea flavonoids, wherein said composition is present in a hydroalcoholic solution.

5. A method of treating excess weight through control of the body weight which comprises administering the composition according to claim 2.

6. A method to treat excess weight through control of body weight which comprises administering the pharmaceutical composition according to claim 4.

7. The method according to claim 6, wherein the administration is oral administration.

8. A method of treating obesity through the control of excess weight which comprises administering the composition according to claim 2.

9. A method of treating obesity through control of excess weight which comprises administering the pharmaceutical composition according to claim 4.

10. The method according to claim 9, wherein the administration is oral administration.

11. A process to produce the composition according to claim 1, comprising the step of suspending N-oleyl-phosphatidyl-ethanolamine under stirring in a hydroalcoholic solution buffered at an acid pH containing green tea bioflavonoids.

12. The process according to claim 11, wherein a resulting emulsion is then dehydrated by spray drying.

13. A pharmaceutical composition comprising the composition according to claim 2.

14. A method to treat excess weight through control of body weight which comprises administering a pharmaceutical composition according to claim 13.

15. The method according to claim 14, wherein the administration is oral administration.

* * * * *